US012637701B2

(12) United States Patent
Nonaka et al.

(10) Patent No.: US 12,637,701 B2
(45) Date of Patent: May 26, 2026

(54) TRANSFORMED CELL HAVING ABILITY TO PRODUCE 2,5-PYRIDINE DICARBOXYLIC ACID

(71) Applicant: Kao Corporation, Tokyo (JP)

(72) Inventors: Kyoshiro Nonaka, Wakayama (JP); Fumikazu Takahashi, Wakayama (JP)

(73) Assignee: KAO CORPORATION, Tokyo (JP)

( * ) Notice: Subject to any disclaimer, the term of this patent is extended or adjusted under 35 U.S.C. 154(b) by 749 days.

(21) Appl. No.: 17/791,377

(22) PCT Filed: Dec. 28, 2020

(86) PCT No.: PCT/JP2020/049104

§ 371 (c)(1),
(2) Date: Jul. 7, 2022

(87) PCT Pub. No.: WO2021/140980

PCT Pub. Date: Jul. 15, 2021

(65) Prior Publication Data

US 2024/0110211 A1 Apr. 4, 2024

(30) Foreign Application Priority Data

Jan. 8, 2020 (JP) ................................ 2020-001628

(51) Int. Cl.

*C12P 13/00* (2006.01)
*C12N 9/02* (2006.01)
*C12N 9/10* (2006.01)
*C12N 9/88* (2006.01)
*C12N 15/70* (2006.01)
*C12P 7/44* (2006.01)
*C12P 17/12* (2006.01)

(52) U.S. Cl.

CPC ............ *C12P 17/12* (2013.01); *C12N 9/0069* (2013.01); *C12N 9/1096* (2013.01); *C12N 9/88* (2013.01); *C12N 15/70* (2013.01); *C12P 7/44* (2013.01); *C12Y 113/11* (2013.01); *C12Y 206/01* (2013.01); *C12Y 401/03038* (2013.01); *C12N 2800/101* (2013.01)

(58) Field of Classification Search

CPC .. C12P 17/12; C12P 7/44; C12P 13/00; C12N 9/0069; C12N 9/1096; C12N 9/88; C12N 15/70; C12N 2800/101; C12N 9/0004; C12N 15/09; C12N 15/74; C12Y 113/11; C12Y 206/01; C12Y 401/03038

See application file for complete search history.

(56) References Cited

U.S. PATENT DOCUMENTS

| | | | |
|---|---|---|---|
| 7,223,572 B1 | 5/2007 | Gunji et al. | |
| 2008/0038825 A1 | 2/2008 | Gunji et al. | |
| 2013/0171700 A1 | 7/2013 | Gunji et al. | |
| 2016/0289711 A1* | 10/2016 | Yunomura ............... | C12N 9/88 |
| 2019/0194629 A1 | 6/2019 | Inui et al. | |
| 2021/0317484 A1 | 10/2021 | Nonaka et al. | |

FOREIGN PATENT DOCUMENTS

| | | | |
|---|---|---|---|
| CN | 1690191 | A | 11/2005 |
| CN | 109153986 | A | 1/2019 |
| JP | 2002-101881 | A | 4/2002 |
| JP | 2009-065839 | A | 4/2009 |
| JP | 2010-207094 | A | 9/2010 |
| JP | 2014-045692 | A | 3/2014 |
| JP | 2018-083789 | A | 5/2018 |
| JP | 2020-39330 | A | 3/2020 |
| WO | WO 2016/202875 | A1 | 12/2016 |
| WO | WO 2017/146241 | A1 | 8/2017 |
| WO | WO 2020/054598 | A1 | 3/2020 |

OTHER PUBLICATIONS

Nierman et al., Complete genome sequence of Caulobacter crescentus, Mar. 20, 2001, Proceedings of the National Academy of Sciences of the United States of America, 98(7), 4136-4141. (Year: 2001).*
International Search Report for PCT/JP2020/049104; I.A. fd Dec. 28, 2020, mailed Feb. 16, 2021, by the Japan Patent Office, Tokyo, Japan.
International Preliminary Report on Patentability (IPRP), Chapter I of the Patent Cooperation Treaty, including the Written Opinion, for PCT/JP2020/049104; I.A. fd Dec. 28, 2020, issued Jul. 12, 2022, by the International Bureau of WIPO, Geneva, Switzerland.
Pellis A, et al., "Enzymatic synthesis of lignin derivable pyridine based polyesters for the substitution of petroleum derived plastics." Nat Commun. Apr. 16, 2019;10(1):1762. doi: 10.1038/s41467-019-09817-3. PMID: 30992443; PMCID: PMC6467960.
Mycroft, Z, et al., "Biocatalytic conversion of lignin to aromatic dicarboxylic acids in *Rhodococcus jostii* RHA1 by re-routing aromatic degradation pathways." Published Jul. 9, 2015; Green Chem., 2015 17:4974-4979.
Vandamme, E J et al., eds, Industrial Biotechnology of Vitamins, Biopigments, and Antixoidants, John Wiley & Sons, ISBN: 978-3-527-33734-Apr. 7, 2016 Section 3.7 "Synthesis," pp. 47-49.

(Continued)

*Primary Examiner* — Sharmila G Landau
*Assistant Examiner* — Ashley T White
(74) *Attorney, Agent, or Firm* — Element IP, PLC

(57) ABSTRACT

Provided are a transformed cell having the ability to produce 2,5-pyridine dicarboxylic acids, and a method for producing 2,5-pyridine dicarboxylic acids using the same. The present invention provides a transformed cell having the ability to produce 2,5-pyridine dicarboxylic acids, the transformed cell being derived from a microbe having the ability to biosynthesize 4-aminobenzoic acids and having the enhanced expression of the following polypeptides (I) and (II): (I) a polypeptide having 4-aminobenzoic acid hydroxylation activity, and (II) a polypeptide having 4-amino-3-hydroxybenzoate 2,3-dioxygenase activity.

17 Claims, No Drawings

Specification includes a Sequence Listing.

(56) References Cited

OTHER PUBLICATIONS

Zeng, M et al., "Novel bimetallic lanthanide metal-organic frameworks (Ln-MOFs) for colour-tuning through energy-transfer between visible and near- infrared emitting $Ln^{3+}$ ions." J. Mater. Chem. C, 2019,7, 2751-2757; Published Feb. 5, 2019.

Zhang, Q et al., "Formation of a Supramolecular Polymeric Adhesive via Water-Participant Hydrogen Bond Formation." J Am Chem Soc. May 22, 2019;141(20):8058-8063. doi: 10.1021/jacs.9b02677. Epub May 14, 2019. PMID: 31066557.

Takenaka, S et al., "A novel meta-cleavage dioxygenase that cleaves a carboxyl-group-substituted 2-aminophenol. Purification and characterization of 4-amino-3-hydroxybenzoate 2,3-dioxygenase from *Bordetella* sp. strain 10d." Eur J Biochem. Dec. 2002;269(23):5871-7. doi: 10.1046/j.1432-1033.2002.03306.x. PMID: 12444975.

Murakami, S et al., "Cloning of a gene encoding 4-amino-3-hydroxybenzoate 2,3-dioxygenase from *Bordetella* sp. 10d." Biochem Biophys Res Commun. Feb. 6, 2004;314(2):489-94. doi: 10.1016/j.bbrc.2003.12.111. PMID: 14733932.

* cited by examiner

TRANSFORMED CELL HAVING ABILITY TO PRODUCE 2,5-PYRIDINE DICARBOXYLIC ACID

REFERENCE TO SEQUENCE LISTING SUBMITTED ELECTRONICALLY

The content of the electronically submitted substitute sequence listing, file name 2537_2180001_SeqListing_ST25.txt, size 31,730 bytes; and date of creation Nov. 22, 2022, filed herewith, is incorporated herein by reference in its entirety.

FIELD OF THE INVENTION

The present invention relates to a transformed cell having the ability to produce 2,5-pyridine dicarboxylic acids and use thereof.

BACKGROUND OF THE INVENTION

The development of methods for producing compounds by biological approaches using renewable resources as starting materials is important for the realization of sustainable society. 2,5-Pyridine dicarboxylic acids (2,5-PDCAs) have a backbone similar to that of terephthalic acid which is produced in large amounts from nonrenewable resources as resin starting materials, and methods for producing 2,5-PDCAs by biological approaches from plant residues are also known. Hence, these compounds are expected as terephthalic acid alternatives obtainable from renewable resources (Patent Literature 1 and Non Patent Literatures 1 and 2). 2,5-Pyridine dicarboxylic acids are also known as precursors of nicotinic acid which is a water-soluble vitamin useful for food and pharmaceutical purposes, and further, also used as starting materials for plant growth promoters, organic light-emitting materials, adhesives, and the like (Patent Literature 2 and Non Patent Literatures 3 to 5).

A method of allowing a *Rhodococcus jostii* RHA1 strain harboring protocatechuate 2,3-dioxygenase to act on lignin is disclosed as a method for biologically producing 2,5-pyridine dicarboxylic acids (Patent Literature 1 and Non Patent Literature 2). However, its productivity is very low, and use of lignin, which nonuniformly contains many kinds of compounds, makes it difficult for this approach to stably produce 2,5-pyridine dicarboxylic acids. Furthermore, it is also necessary to separately add ammonium chloride as a nitrogen source necessary for reaction.

In addition, reaction mediated by 4-amino-3-hydroxybenzoate 2,3-dioxygenase (ahdA) carried by a *Bordetella* sp. 10d strain isolated as a 4-amino-3-hydroxybenzoic acid-utilizing bacterium is known as biological reaction to obtain 2,5-pyridine dicarboxylic acids (Non Patent Literature 6). According to this literature, it was confirmed in purified enzymes that 4-amino-3-hydroxybenzoic acid is oxidatively cleaved into 2-amino-5-carboxymuconic 6-semialdehyde through 4-amino-3-hydroxybenzoate 2,3-dioxygenase, followed by nonenzymatic self-conversion into 2,5-pyridine dicarboxylic acid.

However, in the *Bordetella* sp. 10d strain, 2-amino-5-carboxymuconic 6-semialdehyde is converted into 2-hydroxymuconic 6-semialdehyde through deaminase (ahdB). In actuality, no 2,5-pyridine dicarboxylic acid was detected in a culture solution, resulting in unsuccessful production of 2,5-pyridine dicarboxylic acids. If the production of 2,5-pyridine dicarboxylic acids is attempted using purified 4-amino-3-hydroxybenzoate 2,3-dioxygenase, it is necessary to add 4-amino-3-hydroxybenzoic acids as starting materials. Thus, it is difficult to produce 2,5-pyridine dicarboxylic acids practically from the economic standpoint.

[Patent Literature 1] WO 2016/202875

[Patent Literature 2] JP-A-2018-83789

[Non Patent Literature 1] Alessandro Pellis et al., Nature Communications, Vol. 10, pp. 1762 (2019)

[Non Patent Literature 2] Zoe Mycroft et al., Green Chemistry, Vol. 17, pp. 4974 (2015)

[Non Patent Literature 3] Erick J. Vandamme, Jose Luis Revuelta, Industrial Biotechnology of Vitamins, Biopigments, and Antioxidants (Book), John Wiley & Sons, 2016

[Non Patent Literature 4] Min Zeng et al., Journal of Materials Chemistry C, Vol. 7, pp. 2751 (2019)

[Non Patent Literature 5] Qiao Zhang et al., Journal of the American Chemical Society Vol. 141, pp 8058 (2019)

[Non Patent Literature 6] Shinji Takenaka et al., European Journal of Biochemistry, Vol. 269, pp. 5871 (2002)

SUMMARY OF THE INVENTION

The present invention relates to the following 1) to 2).

1) A transformed cell having ability to produce 2,5-pyridine dicarboxylic acids, the transformed cell being derived from a microbe having ability to biosynthesize 4-aminobenzoic acids and having enhanced expression of the following polypeptides (I) and (II):

(I) a polypeptide having 4-aminobenzoic acid hydroxylation activity, and (II) a polypeptide having 4-amino-3-hydroxybenzoate 2,3-dioxygenase activity.

2) A method for producing 2,5-pyridine dicarboxylic acids or salts thereof, comprising a step of culturing the transformed cell according to 1).

DETAILED DESCRIPTION OF THE INVENTION

The present invention relates to provision of a transformed cell having the ability to produce 2,5-pyridine dicarboxylic acids, and a method for producing 2,5-pyridine dicarboxylic acids using the same.

The present inventors prepared a microbe producing a polypeptide having particular enzyme activity and found that 2,5-pyridine dicarboxylic acids can be efficiently produced using this microbe.

According to the present invention, 2,5-pyridine dicarboxylic acids for use as starting materials for resins, foods, medicaments, plant growth promoters, organic light-emitting materials, adhesives, and the like can be efficiently produced.

In the present invention, the identity of an amino acid sequence or a nucleotide sequence is calculated by the Lipman-Pearson method (Science, 1985, 227: 1435-1441). Specifically, the identity is calculated by analysis with a unit size to compare (ktup) set to 2 using the homology analysis (search homology) program of genetic information processing software GENETYX Ver. 12.

In the present invention, the term "at least 90% identity" in relation to an amino acid sequence or a nucleotide sequence refers to 90% or higher, preferably 95% or higher, more preferably 96% or higher, even more preferably 97% or higher, even more preferably 98% or higher, even more preferably 99, or higher identity.

In the present invention, the term "amino acid sequence derived by having the deletion, substitution, addition, or insertion of one or more amino acids" refers to an amino acid sequence having the deletion, substitution, addition, or insertion of 1 or more and 10 or less, preferably 1 or more and 8 or less, more preferably 1 or more and 5 or less, even more preferably 1 or more and 3 or less amino acids. In the present specification, the term "nucleotide sequence having the deletion, substitution, addition, or insertion of one or more nucleotides" refers to a nucleotide sequence having the deletion, substitution, addition, or insertion of 1 or more and 30 or less, preferably 1 or more and 24 or less, more preferably 1 or more and 15 or less, even more preferably 1 or more and 9 or less nucleotides. In the present specification, the "addition" of an amino acid or a nucleotide includes the addition of an amino acid or a nucleotide to one or both ends of a sequence.

In the present invention, the "operable linkage" of a gene to a control region means that the gene is linked to the control region such that the gene is expressible under the control of the control region. The procedures of the "operable linkage" of a gene to a control region are well known to those skilled in the art.

In the present invention, the term "original" which is used for a function, property, or trait of a cell is used for indicating that the function, the property, or the trait is present in the wild type of the cell. By contrast, the term "foreign" is used for indicating that the function, the property, or the trait is introduced ab extra, not indigenous to the cell. For example, a "foreign" gene or polynucleotide is a gene or a polynucleotide introduced ab extra into a cell. The foreign gene or polynucleotide may be derived from an organism of the same species as that of the cell harboring it or may be derived from an organism of different species therefrom (i.e., a heterologous gene or polynucleotide).

In the present invention, specific examples of the "2,5-pyridine dicarboxylic acids" include 2,5-pyridine dicarboxylic acid derivatives of the following formula (1):

(1)

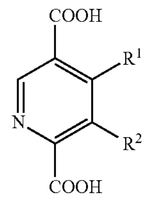

wherein $R^1$ and $R^2$ each independently represent a hydrogen atom, a hydroxy group (—OH), a methoxy group (—$OCH_3$), an amino group (—$NH_2$), a halogen atom, a carboxy group (—COOH), a methyl group (—$CH_3$), or an ethyl group (—$CH_2CH_3$).

The 2,5-pyridine dicarboxylic acid derivatives can be present in the forms of salts. Examples of such salts include salts with alkali metals such as sodium and potassium, and salts with alkaline earth metals such as calcium and magnesium.

Specific examples of the 4-aminobenzoic acids include 4-aminobenzoic acid derivatives of the following formula (2):

(2)

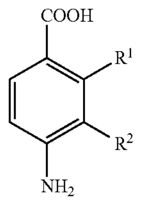

wherein $R^1$ and $R^2$ are as defined above.

In the formula (1) or (2), examples of the halogen atom represented by $R^1$ or $R^2$ include a fluorine atom, a chlorine atom, a bromine atom, and an iodine atom. A fluorine atom is preferred.

Each of $R^1$ and $R^2$ is preferably a hydrogen atom, a hydroxy group (—OH), a methoxy group (—$OCH_3$), a fluorine atom (—F) or a methyl group (—$CH_3$). More preferably, both $R^1$ and $R^2$ are hydrogen atoms.

In the present invention, the "transformed cell having the ability to produce 2,5-pyridine dicarboxylic acids" is a microbial cell which is derived from a microbe having the ability to biosynthesize 4-aminobenzoic acids, and has the enhanced expression of (I) a polypeptide having 4-aminobenzoic acid hydroxylation activity, and (II) a polypeptide having 4-amino-3-hydroxybenzoate 2,3-dioxygenase activity.

Examples of the (I) polypeptide having 4-aminobenzoic acid hydroxylation activity include (A) a polypeptide which consists of the amino acid sequence represented by SEQ ID NO: 2, or a polypeptide which consists of an amino acid sequence having at least 90% identity to the amino acid sequence represented by SEQ ID NO: 2, and has 4-aminobenzoic acid hydroxylation activity, and (B) a polypeptide which consists of the amino acid sequence represented by SEQ ID NO: 4, or a polypeptide which consists of an amino acid sequence having at least 90% identity to the amino acid sequence represented by SEQ ID NO: 4, and has 4-aminobenzoic acid hydroxylation activity.

In this context, the polypeptide which consists of the amino acid sequence represented by SEQ ID NO: 2 (also referred to as "HFM122") and the polypeptide which consists of the amino acid sequence represented by SEQ ID NO: 4 (also referred to as "HFM689") are each known as 4-hydroxybenzoate 3-monooxygenase (EC1.14.13.2). The 4-hydroxybenzoate 3-monooxygenase is an enzyme having catalytic activity of accelerating any one or both of reaction to produce protocatechuic acid by hydroxylating position 3 of 4-hydroxybenzoic acid and inverse reaction thereof, and is an enzyme which catalyzes the hydroxylation of 4-hydroxybenzoic acids (4-hydroxybenzoate hydroxylase).

The 4-hydroxybenzoate 3-monooxygenase is known to have activity of catalyzing the hydroxylation of position 3 of its original substrate 4-hydroxybenzoic acid as well as 4-aminobenzoic acid having a molecular structure similar thereto (e.g., Domenico L. Gatti et al., Biochemistry, Vol. 35, No. 2, pp. 567-578 (1996)). The present applicant found that these enzymes HFM122 and HFM689 have activity of catalyzing the hydroxylation of 4-aminobenzoic acids, preferably activity of catalyzing the hydroxylation of position 3 of 4-aminobenzoic acids (Japanese Patent Application No. 2018-171849). Thus, in the present invention, the "4-aminobenzoic acid hydroxylation activity" means activity of catalyzing the hydroxylation of 4-aminobenzoic acids, preferably activity of catalyzing the hydroxylation of position 3 of 4-aminobenzoic acids.

This 4-aminobenzoic acid hydroxylation activity can be determined by, for example, a method described in Japanese Patent Application No. 2018-171849.

Examples of the amino acid sequence having at least 90% identity to the amino acid sequence represented by SEQ ID NO: 2 or 4 include an amino acid sequence consisting of the amino acid sequence represented by SEQ ID NO: 2 or 4 but having the deletion, substitution, addition, or insertion of one or more amino acids.

Examples of the (II) polypeptide having 4-amino-3-hydroxybenzoate 2,3-dioxygenase activity include (C) a polypeptide which consists of the amino acid sequence represented by SEQ ID NO: 6, or a polypeptide which consists of an amino acid sequence having at least 90% identity to the amino acid sequence represented by SEQ ID NO: 6, and has 4-amino-3-hydroxybenzoate 2,3-dioxygenase activity.

The polypeptide which consists of the amino acid sequence represented by SEQ ID NO: 6 is known as 4-amino-3-hydroxybenzoate 2,3-dioxygenase. The 4-amino-3-hydroxybenzoate 2,3-dioxygenase is an enzyme which oxidatively cleaves the benzene ring of 4-amino-3-hydroxybenzoic acid to form 2-amino-5-carboxymuconic 6-semialdehyde. The 4-amino-3-hydroxybenzoate 2,3-dioxygenase activity can be determined by, for example, a method known in the art (Non Patent Literature 6 described above)).

Examples of the amino acid sequence having at least 90% identity to the amino acid sequence represented by SEQ ID NO: 6 include an amino acid sequence consisting of the amino acid sequence represented by SEQ ID NO: 6 but having the deletion, substitution, addition, or insertion of one or more amino acids.

Examples of a method for introducing a mutation such as deletion, substitution, addition, or insertion of an amino acid to the amino acid sequence of any of the polypeptides include a method of introducing a mutation such as deletion, substitution, addition, or insertion of a nucleotide to a nucleotide sequence encoding the amino acid sequence. Examples of an approach for introducing a mutation to the nucleotide sequence include mutagenesis with a chemical mutagen such as ethyl methanesulfonate, N-methyl-N-nitrosoguanidine, or nitrous acid or with a physical mutagen such as ultraviolet ray, X ray, gamma ray, or ion beam, site-directed mutagenesis, and a method described by Dieffenbach et al. (Cold Spring Harbor Laboratory Press, New York, 581-621, 1995). Examples of the site-directed mutagenesis approach include a method using splicing overlap extension (SOE) PCR (Horton et al., Gene 77, 61-68, 1989), ODA method (Hashimoto-Gotoh et al., Gene, 152, 271-276, 1995), and Kunkel method (Kunkel, T. A., Proc. Natl. Acad. Sci. USA, 1985, 82, 488). Alternatively, a commercially available kit for site-directed mutagenesis such as Site-Directed Mutagenesis System Mutan-Super Express Km kit (Takara Bio Inc.), Transformer™ Site-Directed Mutagenesis kit (Clontech Laboratories, Inc.), or KOD-Plus-Mutagenesis Kit (Toyobo Co., Ltd.) may be used.

In the present invention, the transformed cell having the enhanced expression of the polypeptide having 4-aminobenzoic acid hydroxylation activity, and the polypeptide having 4-amino-3-hydroxybenzoate 2,3-dioxygenase activity can be a host cell containing, in an expressible state, polynucleotides necessary for the expression of the polypeptides. The polynucleotides may be foreign ones or may be the original ones of the cell. Examples thereof include cells expressibly harboring the polynucleotides, and cells having enhanced degrees of expression of the polynucleotides. Specific examples thereof include cells harboring vectors or DNA fragments containing the polynucleotides and control regions operably linked thereto, and cells having strong control regions replaced for the control regions of the polynucleotides.

In this context, for the polynucleotides, examples of (i) a polynucleotide encoding the polypeptide having 4-aminobenzoic acid hydroxylation activity include the following polynucleotides (a) and (b), and examples of (ii) a polynucleotide encoding the polypeptide having 4-amino-3-hydroxybenzoate 2,3-dioxygenase activity include the following polynucleotide (c) (these polynucleotides are also collectively referred to as the "polynucleotide of the present invention"):

(a) a polynucleotide which consists of the nucleotide sequence represented by SEQ ID NO: 1, or a polynucleotide which consists of a nucleotide sequence having at least 90% identity to the nucleotide sequence represented by SEQ ID NO: 1, and encodes the polypeptide having 4-aminobenzoic acid hydroxylation activity;

(b) a polynucleotide which consists of the nucleotide sequence represented by SEQ ID NO: 3, or a polynucleotide which consists of a nucleotide sequence having at least 90% identity to the nucleotide sequence represented by SEQ ID NO: 3, and encodes the polypeptide having 4-aminobenzoic acid hydroxylation activity; and (c) a polynucleotide which consists of the nucleotide sequence represented by SEQ ID NO: 5, or a polynucleotide which consists of a nucleotide sequence having at least 90% identity to the nucleotide sequence represented by SEQ ID NO: 5, and encodes the polypeptide having 4-amino-3-hydroxybenzoate 2,3-dioxygenase activity.

Examples of the nucleotide sequence having at least 90% identity to the nucleotide sequence represented by SEQ ID NO: 1, 3 or 5 include a nucleotide sequence consisting of the nucleotide sequence represented by SEQ ID NO: 1, 3 or 5 but having the deletion, substitution, addition, or insertion of one or more nucleotides. The method for introducing a mutation such as deletion, substitution, addition, or insertion of a nucleotide to the nucleotide sequence is as mentioned above. The polynucleotide may be in a single-stranded or double-stranded form, or may be DNA or RNA. The DNA may be cDNA or artificial DNA such as chemically synthesized DNA.

The polynucleotide may be incorporated into a vector. Preferably, the vector containing the polynucleotide of the present invention is an expression vector. Preferably, the vector is an expression vector which can transfer the polynucleotide of the present invention into a host microbe and enables the polynucleotide to be expressed within the host microbe. Preferably, the vector contains the polynucleotide of the present invention, and a control region operably linked thereto. The vector may be a vector capable of proliferating and replicating autonomously outside the chromosome (i.e., in a plasmid), or may be a vector which is incorporated into the chromosome.

Specific examples of the vector include pBluescript II SK(−) (Stratagene California), pUC series vectors such as pUC18/19 and pUC118/119 (Takara Bio Inc.), pET series vectors (Takara Bio Inc.), pGEX series vectors (GE Healthcare Japan Corp.), pCold series vectors (Takara Bio Inc.), pHY300PLK (Takara Bio Inc.), pUB110 (Mckenzie, T. et al., 1986, Plasmid 15 (2): 93-103), pBR322 (Takara Bio Inc.), pRS403 (Stratagene California), pMW218/219 (Nippon Gene Co., Ltd.), pRI series vectors such as pRI909/910 (Takara Bio Inc.), pBI series vectors (Clontech Laboratories, Inc.), IN3 series vectors (Inplanta Innovations Inc.), pPTR1/2 (Takara Bio Inc.), pDJB2 (D. J. Ballance et al., Gene, 36, 321-331, 1985), pAB4-1 (van Hartingsveldt W et al., Mol Gen Genet, 206, 71-75, 1987), pLeu4 (M. I. G. Roncero et al., Gene, 84, 335-343, 1989), pPyr225 (C. D. Skory et al., Mol Genet Genomics, 268, 397-406, 2002), and pFG1 (Gruber, F. et al., Curr Genet, 18, 447-451, 1990).

The polynucleotide may be constructed as a DNA fragment containing the same. Examples of the DNA fragment include PCR-amplified DNA fragments and restriction enzyme-cleaved DNA fragments. Preferably, the DNA fragment can be an expression cassette containing the polynucleotide of the present invention, and a control region operably linked thereto.

The control region contained in the vector or the DNA fragment is a sequence for allowing the polynucleotide of the present invention to be expressed within a host cell into which the vector or the DNA fragment has been introduced. Examples thereof include expression regulation regions such as promoters and terminators, and replication origins. The type of the control region can be appropriately selected according to the type of the host microbe into which the vector or the DNA fragment is introduced. If necessary, the vector or the DNA fragment may further have a selective marker such as an antibiotic resistance gene or an amino acid synthesis-related gene.

A general genetic transformation method, for example, electroporation, transformation, transfection, conjugation, protoplast method, particle gun method, or *Agrobacterium* method, can be used for transferring the vector or the DNA fragment into the host cell.

The transformed cell harboring the vector or the DNA fragment of interest can be selected by using the selective marker. When the selective marker is, for example, an antibiotic resistance gene, the cell harboring the vector or the DNA fragment of interest can be selected by culture in a culture medium supplemented with the antibiotic. When the selective marker is, for example, an amino acid synthesis-related gene, the cell harboring the vector or the DNA fragment of interest can be selected by using the presence or absence of the amino acid auxotrophy as an index after gene transfer into the host cell requiring the amino acid. Alternatively, the transfer of the vector or the DNA fragment of interest may be confirmed by examining the DNA sequence of the transformed cell by PCR or the like.

Examples of the strong control region include, but are not particularly limited to, high-expression promoters known in the art such as T7 promoter, lac promoter, tac promoter, trp promoter, tu promoter, and gap promoter.

Examples of the method for replacing the strong control region for the control region of the polynucleotide present on the genome of the host cell include a method of introducing a DNA fragment containing the polynucleotide sequences of the strong control region and a selective marker into the host cell, and selecting a transformed cell by homologous recombination or nonhomologous recombination.

In the present invention, a microbe having the ability to biosynthesize 4-aminobenzoic acids is used as the host cell. Any of cells of a fungi, a yeast, actinomycete, *E. coli*, *Bacillus subtilis*, or the like may be used as the microbe, and *E. coli* or actinomycete is preferred. Examples of the actinomycete include bacteria of the genus *Corynebacterium*, bacteria of the genus *Mycobacterium*, bacteria of the genus *Rhodococcus*, bacteria of the genus *Streptomyces*, and bacteria of the genus *Propionibacterium*. A bacterium of the genus *Corynebacterium* is preferred, and *Corynebacterium glutamicum* is more preferred.

The phrase "having the ability to biosynthesize 4-aminobenzoic acids" means that the microbe needs only to be able to supply 4-aminobenzoic acids. A microbe having enhanced ability to supply 4-aminobenzoic acids is more preferred. Examples of the method for enhancing the ability of the microbe to supply 4-aminobenzoic acids include a method of introducing, into a cell, a vector containing a polynucleotide encoding a polypeptide necessary for biosynthesizing 4-aminobenzoic acids, and a control region operably linked thereto, and a method of substituting the control region of a polynucleotide encoding a polypeptide necessary for biosynthesizing 4-aminobenzoic acids, which is originally carried by a cell, with a strong control region.

In this context, examples of the polypeptide necessary for biosynthesizing 4-aminobenzoic acids include (III) 4-amino-4-deoxychorismate synthase and (IV) 4-amino-4-deoxychorismate lyase. Thus, examples of the enhanced ability to supply 4-aminobenzoic acids include an aspect in which the expression of any one or more of these enzymes is enhanced.

Specific examples thereof include a method of introducing a vector or a DNA fragment containing one or more polynucleotides selected from the group consisting of (iii) a polynucleotide (e.g., SEQ ID NO: 7) encoding the 4-amino-4-deoxychorismate synthase and (iv) a polynucleotide (e.g., SEQ ID NO: 8) encoding the 4-amino-4-deoxychorismate lyase, and a control region operably linked thereto into a microbe, and a method of replacing a strong control region for one or more control regions of any of the above polynucleotides, which are originally carried by the microbe.

The method for introduction of the vector containing the polynucleotide of interest and the method for replacement of a strong control region for a control region can be performed in the same manner as the methods described above.

The transformed cell of the present invention thus prepared is cultured and evaluated for its productivity of 2,5-pyridine dicarboxylic acids, and a proper transformed cell can be selected to obtain a strain producing useful 2,5-pyridine dicarboxylic acids. Methods for measuring products can be performed in accordance with methods described in Reference Examples mentioned later.

The method for producing 2,5-pyridine dicarboxylic acids or salts thereof according to the present invention is carried out by culturing the transformed cell mentioned above in a proper culture medium. The culture conditions can be appropriately designed depending on the microbe used.

Any of a natural culture medium and a synthetic culture medium may be used as the culture medium for the culture of the transformed cell as long as the culture medium contains a carbon source, a nitrogen source, inorganic salts, etc. and permits efficient culture of the transformed cell of the present invention. For example, saccharides such as glucose, polyols such as glycerin, alcohols such as ethanol, or organic acids such as pyruvic acid, succinic acid or citric acid can be used as carbon sources. Preferred examples thereof include saccharides such as glucose, maltose, sucrose, fructose, and materials containing them.

For example, peptone, meat extracts, yeast extracts, casein hydrolysates, alkali extracts of soymeal, alkylamines such as methylamine, or ammonia or its salt can be used as nitrogen sources.

In addition, phosphate, carbonate, sulfate, salts of magnesium, calcium, potassium, iron, manganese, zinc, or the like, a particular amino acid, a particular vitamin, an anti-foaming agent, etc. may be used, if necessary.

The culture can usually be performed, at 10° C. to 40° C. for 6 hours to 72 hours, preferably for 9 hours to 60 hours, more preferably for 12 hours to 48 hours, if necessary, with stirring or shaking. During the culture, an antibiotic such as ampicillin or kanamycin may be added, if necessary, to the culture medium.

The methods for collecting and purifying 2,5-pyridine dicarboxylic acids from the cultures are not particularly limited. Specifically, the collection and the purification can be carried out by combining a well-known ion-exchange resin method, precipitation method, crystallization method, recrystallization method, concentration method and other methods. For example, after removal of bacterial cells by centrifugation or the like, ionic substances are removed with cation- and anion-exchange resins, and the resultant can be concentrated to obtain 2,5-pyridine dicarboxylic acids. 2,5-Pyridine dicarboxylic acids accumulated in the cultures may be used directly without being isolated.

In relation to the embodiments mentioned above, the present invention further discloses the following aspects.

<1> A transformed cell having ability to produce 2,5-pyridine dicarboxylic acids, the transformed cell being derived from a microbe having ability to biosynthesize 4-aminobenzoic acids and having enhanced expression of the following polypeptides (I) and (II):

(I) a polypeptide having 4-aminobenzoic acid hydroxylation activity, and (II) a polypeptide having 4-amino-3-hydroxybenzoate 2,3-dioxygenase activity.

<2> The transformed cell according to <1>, wherein the (I) polypeptide having 4-aminobenzoic acid hydroxylation activity is (A) a polypeptide which consists of the amino acid sequence represented by SEQ ID NO: 2, or a polypeptide which consists of an amino acid sequence having at least 90% identity to the amino acid sequence represented by SEQ ID NO: 2, and has 4-aminobenzoic acid hydroxylation activity, or (B) a polypeptide which consists of the amino acid sequence represented by SEQ ID NO: 4, or a polypeptide which consists of an amino acid sequence having at least 90% identity to the amino acid sequence represented by SEQ ID NO: 4, and has 4-aminobenzoic acid hydroxylation activity.

<3> The transformed cell according to <1> or <2>, wherein the (II) polypeptide having 4-amino-3-hydroxybenzoate 2,3-dioxygenase activity is (C) a polypeptide which consists of the amino acid sequence represented by SEQ ID NO: 6, or a polypeptide which consists of an amino acid sequence having at least 90% identity to the amino acid sequence represented by SEQ ID NO: 6, and has 4-amino-3-hydroxybenzoate 2,3-dioxygenase activity.

<4> The transformed cell according to any of <1> to <3>, wherein the microbe having the ability to biosynthesize 4-aminobenzoic acids is a microbe having enhanced expression of one or more enzymes selected from the group consisting of the following (III) and (IV):

(III) 4-amino-4-deoxychorismate synthase, and (IV) 4-amino-4-deoxychorismate lyase.

<5> The transformed cell according to any of <1> to <4>, wherein the transformed cell is *E. coli* or a bacterium of the genus *Corynebacterium*.

<6> The transformed cell according to <5>, wherein the bacterium of the genus *Corynebacterium* is *Corynebacterium glutamicum*.

<7> A method for producing 2,5-pyridine dicarboxylic acids or salts thereof, comprising a step of culturing a transformed cell according to any of <1> to <6>.

<8> The method according to <7>, wherein the culture is performed in a culture medium containing a saccharide as a carbon source.

<9> The method according to <7> or <8>, further comprising a step of collecting 2,5-pyridine dicarboxylic acids or salts thereof from the cultures.

<10> The method according to any of <6> to <8>, wherein the 2,5-pyridine dicarboxylic acids are 2,5-pyridine dicarboxylic acid derivatives of the following formula (1):

(1)

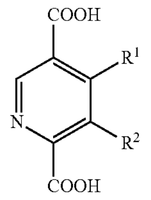

wherein $R^1$ and $R^2$ each independently represent a hydrogen atom, a hydroxy group, a methoxy group, an amino group, a halogen atom, a carboxy group, a methyl group, or an ethyl group, and the 4-aminobenzoic acids are 4-aminobenzoic acid derivatives of the following formula (2):

(2)

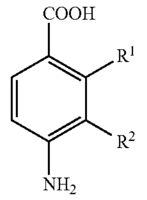

wherein $R^1$ and $R^2$ are as defined above.

<11> The method according to <10>, wherein in the formulas (1) and (2), both $R^1$ and $R^2$ are hydrogen atoms.

EXAMPLES

Hereinafter, the present invention will be described in more detail with reference to Examples. However, the present invention is not limited thereto.

Example 1 Production of 2,5-pyridine dicarboxylic acid

In the following Example, PCR was performed using PrimeSTAR Max Premix (Takara Bio Inc.), unless otherwise specified.

(1) Preparation of Plasmid for 2,5-pyridine Dicarboxylic Acid Production (a) Preparation of Plasmid pECsf_gapS_pabABC A DNA fragment containing a gene encoding 4-amino-4-deoxychorismate synthase and a gene encoding 4-amino- 4-deoxychorismate lyase was amplified by PCR using the genome extracted from a *Corynebacterium glutamicum* ATCC13032 strain by a routine method as a template and using primers GN14_127 (SEQ ID NO: 9, TATTAATTAAATGCGCGTTTTAATTATTGATAATTATGATTC) and GN14_133 (SEQ ID NO: 10, TTGCGGCCGCTTGTTTAAACCTCCTTACAGAAAAATGGTTGGGCG). This fragment was inserted between the PacI site and the NotI site of a plasmid pECsf_gapS (see JP-A-2016-146779) to obtain a plasmid pECsf_gapS_pabABC.

(b) Preparation of Plasmid pECsf_gapS_pabABC HFM122

A DNA fragment for a vector was synthesized by PCR using the plasmid pECsf_gapS_pabABC obtained above as a template and using primers pabABCcory vec R (SEQ ID NO: 11, AAATTTAAACCTCCTTTACAGAAAAATGGTTGG) and pabABCcory vec F (SEQ ID NO: 12, GGAGGTTTAAACAAGCGGCCGCGATATC). Subsequently, a plasmid containing a gene (SEQ ID NO: 1) encoding a polypeptide HFM122 having 4-aminobenzoic acid hydroxylation activity was prepared by artificial gene synthesis, and a DNA fragment for an insert was synthesized by PCR using this plasmid as a template and using primers pECsfD HFM122 F (SEQ ID NO: 13, AGGAGGTTTAAATTTATGCGCACTCAGGTGGCTAT) and pECsfD HFM122 R (SEQ ID NO: 14, CTTGTTTAAACCTCCTTATACGAGTGGCAGTCCTA). These PCR products were treated with DpnI (Takara Bio Inc.). Then, the respective DNA fragments were purified using NucleoSpin Gel and PCR Clean-up (Takara Bio Inc.) and ligated using In-Fusion HD Cloning Kit (Takara Bio Inc.) to construct a plasmid pECsf_gapS_pabABC HFM122. An ECOS Competent *E. coli* DH5α strain (Nippon Gene Co., Ltd.) was transformed with the obtained plasmid solution. The cell solution was spread over LBKm agar medium (1% Bacto Tryptone, 0.5% yeast extract, 1% NaCl, 50 μg/mL kanamycin sulfate, 1.5% agar) and then left standing overnight at 37° C. The obtained colonies were subjected to PCR reaction using Sapphire Amp (Takara Bio Inc.) and primers pabABC+pobA for CPCR F (SEQ ID NO: 15, GCTATCAAAACATTCGGCACATTGGTTTTCC) and pabABC+pobA for CPCR R (SEQ ID NO: 16, GGAAGATGCGTGATCTGATCCTTCAACTC) to select a transformant confirmed to harbor the DNA fragment of interest. The obtained transformant was inoculated to 2 mL of LBKm liquid medium (1% Bacto Tryptone, 0.5% yeast extract, 1% NaCl, 50 μg/mL kanamycin sulfate) and cultured overnight at 37° C. A plasmid was purified from this culture solution using NucleoSpin Plasmid EasyPure (Takara Bio Inc.).

(c) Preparation of Plasmid pECsf_gapS_pabABC_tuD_HFM122

A DNA fragment for a vector was synthesized by PCR using the plasmid pECsf_gapS_pabABC HFM122 obtained above as a template and using primers pabC last R (SEQ ID NO: 17, TTACAGAAAAATGGTTGGGCGCAA) and HFM122 F (SEQ ID NO: 18, ATGCGCACTCAGGTGGCTATCG). Subsequently, a DNA fragment (SEQ ID NO: 19, TACGTACCTGCAGGTAGCGTGTCAGTAGGCGC GTAGGGTAAGTGGGGTAGCGGCTTG TTAGATATCTTGAAATCGGCTTTCAACAGCATTGATTTCGATGTATTTAGCTGGCCG TTACCCTGCGAATGTCCACAGGGTAGCTGGTAGTTTGAAAATC AACGCCGTTGCCCT TAGGATTCAGTAACTGGCACATTTTGTAATGCGCTAGATCTGTGTGCTCAGTCTTCC AGGCTGCTTATCACAGTGAAAGCAAAACCAATTCGT GGCTGCGAAAGTCGTAGCCAC CACGAAGTCCAAAGGAGGATCTAAATTATGAATAATATAAAAGGAGGAATTAATTAA) containing tuf gene (cg0587) promoter (hereinafter, referred to as tu promoter) carried by a *Corynebacterium glutamicum* ATCC13032 strain was prepared by artificial gene synthesis, and a DNA fragment for an insert was synthesized by PCR using this fragment as a template and using primers pabC-Ptu F (SEQ ID NO: 20, ACCATTTTTCTGTAATACGTACCTGCAGGTAGCGTG) and Ptu-HFM122 R (SEQ ID NO: 21, CACCTGAGTGCGCATTTAATTAATTCCTCCTTTTA). These PCR products were treated with DpnI (Takara Bio Inc.). Then, the respective DNA fragments were purified using NucleoSpin Gel and PCR Clean-up (Takara Bio Inc.) and ligated using In-Fusion HD Cloning Kit (Takara Bio Inc.) to construct a plasmid pECsf_gapS_pabABC_tuD_HFM122. An ECOS Competent *E. coli* DH5α strain (Nippon Gene Co., Ltd.) was transformed with the obtained plasmid solution. The cell solution was spread over LBKm agar medium and then left standing overnight at 37° C. The obtained colonies were subjected to PCR reaction using Sapphire Amp (Takara Bio Inc.) and primers Ptu seq 1 (SEQ ID NO: 22, GCTTGTTAGATATCTTGAAATCGGCTTTC) and pabABC+pobA for CPCR R (SEQ ID NO: 16, GGAAGATGCGTGATCTGATCCTTCAACTC) to select a transformant confirmed to harbor the DNA fragment of interest. The obtained transformant was inoculated to 2 mL of LBKm liquid medium and cultured overnight at 37° C. A plasmid was purified from this culture solution using NucleoSpin Plasmid EasyPure (Takara Bio Inc.).

(d) Preparation of Plasmid pECsf_gapS_pabABC_tu_HFM122

A DNA fragment for a vector was synthesized by PCR using the plasmid pECsf_gapS_pabABC_tuD_HFM122 obtained above as a template and using primers pGapABA_tu vec F (SEQ ID NO: 23, GGAGGTTTAAACAAGCGG) and pGapABA_tu vec R (SEQ ID NO: 24, AATTTAGATCCTCCTTTGGACTTCGTG). Subsequently, a DNA fragment for an insert was synthesized by PCR using a plasmid containing an HFM122-encoding gene (SEQ ID NO: 1) prepared by artificial gene synthesis as a template and using primers HFM122 ins F (SEQ ID NO: 25, AGGAGGATCTAAATTATGCGCACTCAGGTGGCTATC) and HFM122 ins R (SEQ ID NO: 26, CTTGTTTAAACCTCCTTATACGAGTGGCAGTCCTACG). These PCR products were treated with DpnI (Takara Bio Inc.). Then, the respective DNA fragments were purified using NucleoSpin Gel and PCR Clean-up (Takara Bio Inc.) and ligated using In-Fusion HD Cloning Kit (Takara Bio Inc.) to construct a plasmid pECsf_gapS_pabABC_tu_HFM122. An ECOS Competent *E. coli* DH5α strain (Nippon Gene Co., Ltd.) was transformed with the obtained plasmid solution. The cell solution was spread over LBKm agar medium and then left standing overnight at 37° C. The obtained colonies were subjected to PCR reaction using Sapphire Amp (Takara Bio Inc.) and primers Ptu seq 1 (SEQ ID NO: 22, GCTTGTTAGATATCTTGAAATCGGCTTTC) and pabABC+pobA for CPCR R (SEQ ID NO: 16, GGAAGATGCGTGATCTGATCCTTCAACTC) to select a transformant confirmed to harbor the DNA fragment of interest. The obtained transformant was inoculated to 2 mL of LBKm liquid medium and cultured overnight at 37° C. A plasmid was purified from this culture solution using NucleoSpin Plasmid EasyPure (Takara Bio Inc.).

(e) Preparation of Plasmid pECsf_gapS_pabABC_tu_HFM122_ahdA

A DNA fragment for a vector was synthesized by PCR using the plasmid pECsf_gapS_pabABC_tu_HFM122 obtained above as a template and using primers ahdA vec R (SEQ ID NO: 27, CGCTTGTTTAAACCTCCT-TATACGAGTGGCAGTCCTACG) and ahdA vec F (SEQ ID NO: 28, GCCGCGA-TATCGTTGTAAAAAACCCCGCTC). Subsequently, a plasmid containing gene ahdA (SEQ ID NO: 5) encoding a polypeptide having 4-amino-3-hydroxybenzoate 2,3-dioxygenase activity was prepared by artificial gene synthesis, and a DNA fragment for an insert was synthesized by PCR using this plasmid as a template and using primers ahdA ins F (SEQ ID NO: 29, AGGTTTAAACAAGCGATGAT-CATCCTGGAAAACTTCAAGATG) and ahdA ins R (SEQ ID NO: 30, CAACGATATCGCGGCT-TAATCGCGTCCTGGAGCAAC). These PCR products were treated with DpnI (Takara Bio Inc.). Then, the respective DNA fragments were purified using NucleoSpin Gel and PCR Clean-up (Takara Bio Inc.) and ligated using In-Fusion HD Cloning Kit (Takara Bio Inc.) to construct a plasmid pECsf_gapS_pabABC_tu_HFM122 ahdA. An ECOS Competent *E. coli* DH5α strain (Nippon Gene Co., Ltd.) was transformed with the obtained plasmid solution. The cell solution was spread over LBKm agar medium and then left standing overnight at 37° C. The obtained colonies were subjected to PCR reaction using Sapphire Amp (Takara Bio Inc.) and primers Ptu seq 1 (SEQ ID NO: 22, GCTTGT-TAGATATCTTGAAATCGGCTTTC) and pabABC+pobA for CPCR R (SEQ ID NO: 16, GGAAGATGCGTGATCT-GATCCTTCAACTC) to select a transformant confirmed to harbor the DNA fragment of interest. The obtained transformant was inoculated to 2 mL of LBKm liquid medium and cultured overnight at 37° C. A plasmid was purified from this culture solution using NucleoSpin Plasmid EasyPure (Takara Bio Inc.).

In the constructed plasmid, the gene encoding 4-amino-4-deoxychorismate synthase and the gene encoding 4-amino-4-deoxychorismate lyase were linked under the control of gap promoter, and the gene encoding the polypeptide having 4-aminobenzoic acid hydroxylation activity and the gene encoding 4-amino-3-hydroxybenzoate 2,3-dioxygenase were further linked under the control of the tu promoter.

(2) Transfer of Plasmid into Host Cell

A *Corynebacterium glutamicum* DRHG145 strain (see Japanese Patent Application No. 2014-523757) was transformed with a plasmid pECsf_gapS_pabABC_tu_HFM122 ahdA obtained above by electroporation (Bio-Rad Laboratories, Inc.). The obtained transformed cell solution was spread over LBKm agar medium and then left standing at 30° C. for 2 days. The obtained colonies were used as a transformant.

(3) Culture of Transformant

The transformant obtained above was inoculated to 10 mL of CGXII medium (containing 50 μg/mL kanamycin sulfate) shown in Table 3, and cultured at 30° C. for 48 hours. Then, bacterial cells were removed by centrifugation to obtain a culture supernatant. The concentration of 2,5-pyridine dicarboxylic acid in the obtained culture supernatant was quantified in accordance with the method of Reference Example 1.

TABLE 1

| CGXII medium composition (per L) | |
|---|---|
| Glucose | 50 g |
| $(NH_4)_2SO_4$ | 20 g |
| Urea | 5 g |
| $KH_2PO_4$ | 1 g |
| $K_2HPO_4$ | 1 g |
| $MgSO_4 \cdot 7H_2O$ | 0.25 g |
| $CaCl_2 \cdot 2H_2O$ | 10 mg |
| $FeSO_4 \cdot 7H_2O$ | 10 mg |
| $MnSO_4 \cdot 5H_2O$ | 10 mg |
| $ZnSO_4 \cdot 7H_2O$ | 1 mg |
| $CuSO_4 \cdot 5H_2O$ | 0.2 mg |
| $NiCl_2 \cdot 6H_2O$ | 0.02 mg |
| Biotin (pH 7) | 0.2 mg |
| Tryptone | 10 g |

(4) Results

As a result of culture of the transformant, 0.40 g/L of 2,5-pyridine dicarboxylic acid was detected in the culture supernatant, demonstrating that 2,5-pyridine dicarboxylic acid can be produced by using this bacterial strain.

Reference Example 1 Quantification of 2,5-pyridine dicarboxylic acid 2,5-Pyridine dicarboxylic acid was quantified by HPLC. A reaction solution to be subjected to HPLC analysis was appropriately diluted with 0.1% phosphoric acid. Then, insoluble matter was removed using AcroPrep 96-well filter plates (0.2 μm GHP membrane, Nihon Pall Ltd.). The HPLC apparatus used was Chromaster (Hitachi High-Tech Science Corp.). The analytical column used was L-column ODS (4.6 mm I.D.×150 mm, Chemicals Evaluation and Research Institute, Japan). Eluent A was a 0.1% phosphoric acid solution of 0.1 M potassium dihydrogen phosphate, and eluent B was 70% methanol. Gradient elution was performed under conditions involving a flow rate of 1.0 mL/min and a column temperature of 40° C. A UV detector (detection wavelength: 280 nm) was used for the detection of 2,5-pyridine dicarboxylic acid. A concentration calibration curve was prepared using a standard sample [2,5-pyridine dicarboxylic acid (distributor code P0552, Tokyo Chemical Industry Co., Ltd.)]. 2,5-Pyridine dicarboxylic acid was quantified on the basis of the concentration calibration curve.

What is claimed is:

1. A transformed cell comprising:

(I) a foreign polynucleotide encoding a polypeptide having 4-aminobenzoic acid hydroxylation activity, and (II) a foreign polynucleotide encoding a polypeptide having 4-amino-3-hydroxybenzoate 2,3-dioxygenase activity;

wherein the transformed cell biosynthesizes 4-aminobenzoic acids;

wherein the transformed cell produces 2,5-pyridine dicarboxylic acids; and wherein the transformed cell is *E. coli* or a bacterium of the genus *Corynebacterium*.

2. The transformed cell according to claim 1, wherein the (I) polypeptide having 4-aminobenzoic acid hydroxylation activity is (A) a polypeptide which consists of the amino acid sequence of SEQ ID NO: 2, or a polypeptide which consists of an amino acid sequence having at least 90% identity to the amino acid sequence of SEQ ID NO: 2, and has 4-aminobenzoic acid hydroxylation activity, or (B) a polypeptide which consists of the amino acid sequence of SEQ ID NO: 4, or a polypeptide which consists of an amino acid sequence having at least 90% identity to the amino acid sequence of SEQ ID NO: 4, and has 4-aminobenzoic acid hydroxylation activity.

3. The transformed cell according to claim 1, wherein the (II) polypeptide having 4-amino-3-hydroxybenzoate 2,3-dioxygenase activity is (C) a polypeptide which consists of the amino acid sequence of SEQ ID NO: 6, or a polypeptide which consists of an amino acid sequence having at least 90% identity to the amino acid sequence of SEQ ID NO: 6, and has 4-amino-3-hydroxybenzoate 2,3-dioxygenase activity.

4. The transformed cell according to claim 1, wherein the cell further comprises a foreign polynucleotide encoding one or more enzymes selected from the group consisting of the following (III) and (IV):

(III) 4-amino-4-deoxychorismate synthase, and (IV) 4-amino-4-deoxychorismate lyase.

5. A method for producing 2,5-pyridine dicarboxylic acids or salts thereof, comprising a step of culturing the transformed cell according to claim 1.

6. The method according to claim 5, wherein the culture is performed in a culture medium containing a saccharide as a carbon source.

7. The method according to claim 5, further comprising a step of collecting 2,5-pyridine dicarboxylic acids or salts thereof from the culture.

8. The method according to claim 5, wherein the 2,5-pyridine dicarboxylic acids are 2,5-pyridine dicarboxylic acid derivative of the following formula (1):

(1)

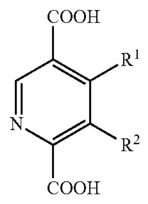

wherein $R^1$ and $R^2$ each independently represent a hydrogen atom, a hydroxy group, a methoxy group, an amino group, a halogen atom, a carboxy group, a methyl group, or an ethyl group, and the 4-aminobenzoic acids are 4-aminobenzoic acid derivatives of the following formula (2):

(2)

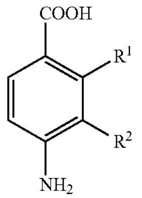

wherein $R^1$ and $R^2$ are as defined above.

9. The transformed cell according to claim 2, wherein the (II) polypeptide having 4-amino-3-hydroxybenzoate 2,3-dioxygenase activity is a polypeptide which consists of the amino acid sequence of SEQ ID NO: 6, or a polypeptide which consists of an amino acid sequence having at least 90% identity to the amino acid sequence of SEQ ID NO: 6, and has 4-amino-3-hydroxybenzoate 2,3-dioxygenase activity.

10. The transformed cell according to claim 2, wherein the cell further comprises a foreign polynucleotide encoding one or more enzymes selected from the group consisting of the following (III) and (IV):

(III) 4-amino-4-deoxychorismate synthase, and (IV) 4-amino-4-deoxychorismate lyase.

11. The transformed cell according to claim 3, wherein the cell further comprises a foreign polynucleotide encoding one or more enzymes selected from the group consisting of the following (III) and (IV):

(III) 4-amino-4-deoxychorismate synthase, and (IV) 4-amino-4-deoxychorismate lyase.

12. A method for producing 2,5-pyridine dicarboxylic acids or salts thereof, comprising a step of culturing the transformed cell according to claim 4.

13. The method according to claim 12, wherein the culture is performed in a culture medium containing a saccharide as a carbon source.

14. The method according to claim 13, further comprising a step of collecting 2,5-pyridine dicarboxylic acids or salts thereof from the culture.

15. The method according to claim 12, wherein the 2,5-pyridine dicarboxylic acids are 2,5-pyridine dicarboxylic acid derivative of the following formula (1):

(1)

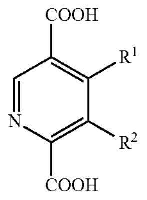

wherein $R^1$ and $R^2$ each independently represent a hydrogen atom, a hydroxy group, a methoxy group, an amino group, a halogen atom, a carboxy group, a methyl group, or an ethyl group, and the 4-aminobenzoic acids are 4-aminobenzoic acid derivatives of the following formula (2):

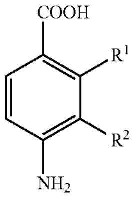

(2)

wherein $R^1$ and $R^2$ are as defined above.

16. The transformed cell according to claim 9, wherein the cell further comprises a foreign polynucleotide encoding one or more enzymes selected from the group consisting of the following (III) and (IV):

(III) 4-amino-4-deoxychorismate synthase, and (IV) 4-amino-4-deoxychorismate lyase.

17. A method for producing 2,5-pyridine dicarboxylic acids or salts thereof, comprising a step of culturing the transformed cell according to claim 16.

* * * * *

SEQUENCE LISTING

```
<160> NUMBER OF SEQ ID NOS: 30

<210> SEQ ID NO 1
<211> LENGTH: 1176
<212> TYPE: DNA
<213> ORGANISM: Caulobacter crescentus
<220> FEATURE:
<221> NAME/KEY: CDS
```

-continued

<222> LOCATION: (1)..(1173)
<223> OTHER INFORMATION: Codon-optimized oligonucleotide

<400> SEQUENCE: 1

```
atg cgc act cag gtg gct atc gta gga gca ggc cca gct ggc ctg ttc       48
Met Arg Thr Gln Val Ala Ile Val Gly Ala Gly Pro Ala Gly Leu Phe
1               5                   10                  15

ttg ggc cat ctc ctc cgt caa gct ggt gtg gac gtc gtg att ctg gaa       96
Leu Gly His Leu Leu Arg Gln Ala Gly Val Asp Val Val Ile Leu Glu
            20                  25                  30

cgc aaa gac cgt gct tat gtc gaa ggc cga gtt cgg gct ggt gtc ctg      144
Arg Lys Asp Arg Ala Tyr Val Glu Gly Arg Val Arg Ala Gly Val Leu
        35                  40                  45

gaa cgt atc acg gtg gag ctg atg gag cgt ctt ggt gtg gat gag cga      192
Glu Arg Ile Thr Val Glu Leu Met Glu Arg Leu Gly Val Asp Glu Arg
    50                  55                  60

atg cgc cga gag ggc ttg gtg cat gct ggc gct aat ctt gcg tct gat      240
Met Arg Arg Glu Gly Leu Val His Ala Gly Ala Asn Leu Ala Ser Asp
65                  70                  75                  80

ggc gag atg ttc cgt atc gac atg gca gag ctc acg ggt ggt tcc acc      288
Gly Glu Met Phe Arg Ile Asp Met Ala Glu Leu Thr Gly Gly Ser Thr
                85                  90                  95

gtc atg gtt tac ggc caa cag gag gtg atg aag gac ctg ttt gat gca      336
Val Met Val Tyr Gly Gln Gln Glu Val Met Lys Asp Leu Phe Asp Ala
            100                 105                 110

gca gag cag cgc gat ctg cga att gtc ttt gac gcc gat gca gtg cgt      384
Ala Glu Gln Arg Asp Leu Arg Ile Val Phe Asp Ala Asp Ala Val Arg
        115                 120                 125

ctg cac gat gtg gaa ggc gaa cgt cct cac atc acc tgg cgc aaa gac      432
Leu His Asp Val Glu Gly Glu Arg Pro His Ile Thr Trp Arg Lys Asp
    130                 135                 140

ggg gca gaa cac cgc ctg gac tgc gat ttc att gcc ggc tgc gac ggc      480
Gly Ala Glu His Arg Leu Asp Cys Asp Phe Ile Ala Gly Cys Asp Gly
145                 150                 155                 160

tac cac gga gtt tct cgt gcg acc att ccc gat aag gtt ctc aag acc      528
Tyr His Gly Val Ser Arg Ala Thr Ile Pro Asp Lys Val Leu Lys Thr
                165                 170                 175

ttc gaa cgg gtg tat ccc ttt ggg tgg ttg gga atc ctg gct gaa gca      576
Phe Glu Arg Val Tyr Pro Phe Gly Trp Leu Gly Ile Leu Ala Glu Ala
            180                 185                 190

cct ccg tgt gac cac gag ttg atc tac tcg aac cat gat cgc ggt ttt      624
Pro Pro Cys Asp His Glu Leu Ile Tyr Ser Asn His Asp Arg Gly Phe
        195                 200                 205

gcc ctg gcg tcg atg cgc tca ccg aca cgc tcc cgc tat tac gtg cag      672
Ala Leu Ala Ser Met Arg Ser Pro Thr Arg Ser Arg Tyr Tyr Val Gln
    210                 215                 220

tgc tca ctc gac gat cgc ctc gag gat tgg tcc gat gaa cgg ttc tgg      720
Cys Ser Leu Asp Asp Arg Leu Glu Asp Trp Ser Asp Glu Arg Phe Trp
225                 230                 235                 240

gat gaa gtt tcg gtt cgc ctg gga ccg gaa gca gcc gct cgg atc gtt      768
Asp Glu Val Ser Val Arg Leu Gly Pro Glu Ala Ala Ala Arg Ile Val
                245                 250                 255

cgc gca cct tcc ttc gag aag agc att gcc cca ctt cgc tcc ttc gtt      816
Arg Ala Pro Ser Phe Glu Lys Ser Ile Ala Pro Leu Arg Ser Phe Val
            260                 265                 270

tcc gag cct atg cgg tat ggc cgc ctt ttc ctc gcg ggt gat gcg gct      864
Ser Glu Pro Met Arg Tyr Gly Arg Leu Phe Leu Ala Gly Asp Ala Ala
        275                 280                 285

cat atc gtt cca ccc act gga gcg aaa ggg atg aac ttg gcc gta tca      912
His Ile Val Pro Pro Thr Gly Ala Lys Gly Met Asn Leu Ala Val Ser
```

```
    290                 295                 300

gac gtc atc atg ctg tcc gaa gcc ctg gtc gaa cac tac cac gaa cgc      960
Asp Val Ile Met Leu Ser Glu Ala Leu Val Glu His Tyr His Glu Arg
305                 310                 315                 320

tct tcc gct ggt atc gat ggt tac agc gca cgt gca ctt gcc cgc gtc     1008
Ser Ser Ala Gly Ile Asp Gly Tyr Ser Ala Arg Ala Leu Ala Arg Val
                325                 330                 335

tgg aag gcg gag cgt ttc agc tgg tgg ttt acc tcc ctt act cac cgc     1056
Trp Lys Ala Glu Arg Phe Ser Trp Trp Phe Thr Ser Leu Thr His Arg
            340                 345                 350

ttc cca gac cag gac ggc ttc gac cgc aag atg caa gtc gcc gaa ttg     1104
Phe Pro Asp Gln Asp Gly Phe Asp Arg Lys Met Gln Val Ala Glu Leu
        355                 360                 365

gca tac atc aag ggt tct cgc gct gcc cag gtc acc ctg gcg gag aac     1152
Ala Tyr Ile Lys Gly Ser Arg Ala Ala Gln Val Thr Leu Ala Glu Asn
    370                 375                 380

tac gta gga ctg cca ctc gta taa                                     1176
Tyr Val Gly Leu Pro Leu Val
385                 390


<210> SEQ ID NO 2
<211> LENGTH: 391
<212> TYPE: PRT
<213> ORGANISM: Caulobacter crescentus

<400> SEQUENCE: 2

Met Arg Thr Gln Val Ala Ile Val Gly Ala Gly Pro Ala Gly Leu Phe
1               5                   10                  15

Leu Gly His Leu Leu Arg Gln Ala Gly Val Asp Val Val Ile Leu Glu
            20                  25                  30

Arg Lys Asp Arg Ala Tyr Val Glu Gly Arg Val Arg Ala Gly Val Leu
        35                  40                  45

Glu Arg Ile Thr Val Glu Leu Met Glu Arg Leu Gly Val Asp Glu Arg
    50                  55                  60

Met Arg Arg Glu Gly Leu Val His Ala Gly Ala Asn Leu Ala Ser Asp
65                  70                  75                  80

Gly Glu Met Phe Arg Ile Asp Met Ala Glu Leu Thr Gly Gly Ser Thr
                85                  90                  95

Val Met Val Tyr Gly Gln Gln Glu Val Met Lys Asp Leu Phe Asp Ala
            100                 105                 110

Ala Glu Gln Arg Asp Leu Arg Ile Val Phe Asp Ala Asp Ala Val Arg
        115                 120                 125

Leu His Asp Val Glu Gly Glu Arg Pro His Ile Thr Trp Arg Lys Asp
    130                 135                 140

Gly Ala Glu His Arg Leu Asp Cys Asp Phe Ile Ala Gly Cys Asp Gly
145                 150                 155                 160

Tyr His Gly Val Ser Arg Ala Thr Ile Pro Asp Lys Val Leu Lys Thr
                165                 170                 175

Phe Glu Arg Val Tyr Pro Phe Gly Trp Leu Gly Ile Leu Ala Glu Ala
            180                 185                 190

Pro Pro Cys Asp His Glu Leu Ile Tyr Ser Asn His Asp Arg Gly Phe
        195                 200                 205

Ala Leu Ala Ser Met Arg Ser Pro Thr Arg Ser Arg Tyr Tyr Val Gln
    210                 215                 220

Cys Ser Leu Asp Asp Arg Leu Glu Asp Trp Ser Asp Glu Arg Phe Trp
225                 230                 235                 240
```

-continued

```
Asp Glu Val Ser Val Arg Leu Gly Pro Glu Ala Ala Ala Arg Ile Val
                245                 250                 255

Arg Ala Pro Ser Phe Glu Lys Ser Ile Ala Pro Leu Arg Ser Phe Val
            260                 265                 270

Ser Glu Pro Met Arg Tyr Gly Arg Leu Phe Leu Ala Gly Asp Ala Ala
        275                 280                 285

His Ile Val Pro Pro Thr Gly Ala Lys Gly Met Asn Leu Ala Val Ser
    290                 295                 300

Asp Val Ile Met Leu Ser Glu Ala Leu Val Glu His Tyr His Glu Arg
305                 310                 315                 320

Ser Ser Ala Gly Ile Asp Gly Tyr Ser Ala Arg Ala Leu Ala Arg Val
                325                 330                 335

Trp Lys Ala Glu Arg Phe Ser Trp Trp Phe Thr Ser Leu Thr His Arg
            340                 345                 350

Phe Pro Asp Gln Asp Gly Phe Asp Arg Lys Met Gln Val Ala Glu Leu
        355                 360                 365

Ala Tyr Ile Lys Gly Ser Arg Ala Ala Gln Val Thr Leu Ala Glu Asn
    370                 375                 380

Tyr Val Gly Leu Pro Leu Val
385                 390


<210> SEQ ID NO 3
<211> LENGTH: 1170
<212> TYPE: DNA
<213> ORGANISM: Novosphingobium aromaticivorans
<220> FEATURE:
<221> NAME/KEY: CDS
<222> LOCATION: (1)..(1167)
<223> OTHER INFORMATION: Codon-optimized oligonucleotide

<400> SEQUENCE: 3

atg aaa acc cag gtt gcc atc att ggt gca gga cca gca ggc ttg ttg       48
Met Lys Thr Gln Val Ala Ile Ile Gly Ala Gly Pro Ala Gly Leu Leu
1               5                   10                  15

ctc ggt cac ttg ctc aaa gcc gaa gga atc gac tgc gtg gtg ctg gag       96
Leu Gly His Leu Leu Lys Ala Glu Gly Ile Asp Cys Val Val Leu Glu
            20                  25                  30

cgc caa acg cca gac tac gta ctt gga cgg att cgc gcg ggt gtt ctg      144
Arg Gln Thr Pro Asp Tyr Val Leu Gly Arg Ile Arg Ala Gly Val Leu
        35                  40                  45

gag cag atc acc gtg ggt ctg atg gaa cgt ctt ggc ctg gat gct cga      192
Glu Gln Ile Thr Val Gly Leu Met Glu Arg Leu Gly Leu Asp Ala Arg
    50                  55                  60

ctg aag gct gag ggc ctg gtt gag gag ggc ttt aac ctt gcc gat ggc      240
Leu Lys Ala Glu Gly Leu Val Glu Glu Gly Phe Asn Leu Ala Asp Gly
65                  70                  75                  80

gaa cgc ctc att cgc atc gac gtc gct aac ttg act ggc aag act gtc      288
Glu Arg Leu Ile Arg Ile Asp Val Ala Asn Leu Thr Gly Lys Thr Val
                85                  90                  95

gtg gtg tat ggc cag acc gag atc acc aaa gac ttg atg gac gct gca      336
Val Val Tyr Gly Gln Thr Glu Ile Thr Lys Asp Leu Met Asp Ala Ala
            100                 105                 110

cct gaa cgt ggc ctc cag gtt atc tac ggt gct agc gaa gtg gca ctg      384
Pro Glu Arg Gly Leu Gln Val Ile Tyr Gly Ala Ser Glu Val Ala Leu
        115                 120                 125

ttc gac atc gag tcc gat gcc cct tat gtc acc tac gtc cat gac ggg      432
Phe Asp Ile Glu Ser Asp Ala Pro Tyr Val Thr Tyr Val His Asp Gly
    130                 135                 140

gct cct cgt cga att gat gca cgg ttc atc gtt ggg tgt gac ggc ttt      480
```

-continued

```
Ala Pro Arg Arg Ile Asp Ala Arg Phe Ile Val Gly Cys Asp Gly Phe
145                 150                 155                 160

cac ggt ccg tca cgt aag gcg att ccg gct tcg gtg gcc cgc gaa tac      528
His Gly Pro Ser Arg Lys Ala Ile Pro Ala Ser Val Ala Arg Glu Tyr
                165                 170                 175

gaa cgc gtc tat ccg ttt ggg tgg ctc ggc atc ctc gca gat gtt cca      576
Glu Arg Val Tyr Pro Phe Gly Trp Leu Gly Ile Leu Ala Asp Val Pro
            180                 185                 190

cca tgc aat cac gag ctg atc tac gcc aat cac gaa cgc ggt ttc gcg      624
Pro Cys Asn His Glu Leu Ile Tyr Ala Asn His Glu Arg Gly Phe Ala
        195                 200                 205

ctg gct tcc atg cgt tcc cac acg cgt agc cgc tat tac gta gat gtt      672
Leu Ala Ser Met Arg Ser His Thr Arg Ser Arg Tyr Tyr Val Asp Val
    210                 215                 220

ccc ctc act gag aag gtg gaa gat tgg tct gac gaa cgc att tgg gac      720
Pro Leu Thr Glu Lys Val Glu Asp Trp Ser Asp Glu Arg Ile Trp Asp
225                 230                 235                 240

gaa ctg gca gta cgc ctt ggc ccc gaa gca gcc gct aac atc aca cga      768
Glu Leu Ala Val Arg Leu Gly Pro Glu Ala Ala Ala Asn Ile Thr Arg
                245                 250                 255

ggt cct tcg atc gag aag tcc atc gct ccg ctt cgg tcc tac gtg ttc      816
Gly Pro Ser Ile Glu Lys Ser Ile Ala Pro Leu Arg Ser Tyr Val Phe
            260                 265                 270

gag cca atg cgc cat ggt tcc ctg ctt ctg tgc gga gat gca gcg cac      864
Glu Pro Met Arg His Gly Ser Leu Leu Leu Cys Gly Asp Ala Ala His
        275                 280                 285

att gtc cca cca aca ggc gct aaa ggc ctg aac ttg gcg gcc tct gat      912
Ile Val Pro Pro Thr Gly Ala Lys Gly Leu Asn Leu Ala Ala Ser Asp
    290                 295                 300

gtg cac tat gcg gca gaa gca ctg acc gga ttc ttc aag cgc gca gat      960
Val His Tyr Ala Ala Glu Ala Leu Thr Gly Phe Phe Lys Arg Ala Asp
305                 310                 315                 320

aac gat gca gtt ccg cgt tac agc gcc aaa gcg ctt gct cgg gtt tgg     1008
Asn Asp Ala Val Pro Arg Tyr Ser Ala Lys Ala Leu Ala Arg Val Trp
                325                 330                 335

aag tct gaa cgc ttc tcc tgg tca ctg acc aag ctc atg cat cgc ttc     1056
Lys Ser Glu Arg Phe Ser Trp Ser Leu Thr Lys Leu Met His Arg Phe
            340                 345                 350

cct gag gac gga ccc ttt gaa cgt gcc atg caa gtc gca gag ctc gag     1104
Pro Glu Asp Gly Pro Phe Glu Arg Ala Met Gln Val Ala Glu Leu Glu
        355                 360                 365

tac atc gcg acc tcc aag gct gcg cag acc tct atc gcc gag aac tac     1152
Tyr Ile Ala Thr Ser Lys Ala Ala Gln Thr Ser Ile Ala Glu Asn Tyr
    370                 375                 380

gtc ggt ctg ccc gtc taa                                             1170
Val Gly Leu Pro Val
385


<210> SEQ ID NO 4
<211> LENGTH: 389
<212> TYPE: PRT
<213> ORGANISM: Novosphingobium aromaticivorans

<400> SEQUENCE: 4

Met Lys Thr Gln Val Ala Ile Ile Gly Ala Gly Pro Ala Gly Leu Leu
1               5                   10                  15

Leu Gly His Leu Leu Lys Ala Glu Gly Ile Asp Cys Val Val Leu Glu
            20                  25                  30

Arg Gln Thr Pro Asp Tyr Val Leu Gly Arg Ile Arg Ala Gly Val Leu
        35                  40                  45
```

-continued

```
Glu Gln Ile Thr Val Gly Leu Met Glu Arg Leu Gly Leu Asp Ala Arg
    50                  55                  60

Leu Lys Ala Glu Gly Leu Val Glu Glu Gly Phe Asn Leu Ala Asp Gly
65                  70                  75                  80

Glu Arg Leu Ile Arg Ile Asp Val Ala Asn Leu Thr Gly Lys Thr Val
                85                  90                  95

Val Val Tyr Gly Gln Thr Glu Ile Thr Lys Asp Leu Met Asp Ala Ala
            100                 105                 110

Pro Glu Arg Gly Leu Gln Val Ile Tyr Gly Ala Ser Glu Val Ala Leu
        115                 120                 125

Phe Asp Ile Glu Ser Asp Ala Pro Tyr Val Thr Tyr Val His Asp Gly
    130                 135                 140

Ala Pro Arg Arg Ile Asp Ala Arg Phe Ile Val Gly Cys Asp Gly Phe
145                 150                 155                 160

His Gly Pro Ser Arg Lys Ala Ile Pro Ala Ser Val Ala Arg Glu Tyr
                165                 170                 175

Glu Arg Val Tyr Pro Phe Gly Trp Leu Gly Ile Leu Ala Asp Val Pro
            180                 185                 190

Pro Cys Asn His Glu Leu Ile Tyr Ala Asn His Glu Arg Gly Phe Ala
        195                 200                 205

Leu Ala Ser Met Arg Ser His Thr Arg Ser Arg Tyr Tyr Val Asp Val
    210                 215                 220

Pro Leu Thr Glu Lys Val Glu Asp Trp Ser Asp Glu Arg Ile Trp Asp
225                 230                 235                 240

Glu Leu Ala Val Arg Leu Gly Pro Glu Ala Ala Ala Asn Ile Thr Arg
                245                 250                 255

Gly Pro Ser Ile Glu Lys Ser Ile Ala Pro Leu Arg Ser Tyr Val Phe
            260                 265                 270

Glu Pro Met Arg His Gly Ser Leu Leu Leu Cys Gly Asp Ala Ala His
        275                 280                 285

Ile Val Pro Pro Thr Gly Ala Lys Gly Leu Asn Leu Ala Ala Ser Asp
    290                 295                 300

Val His Tyr Ala Ala Glu Ala Leu Thr Gly Phe Phe Lys Arg Ala Asp
305                 310                 315                 320

Asn Asp Ala Val Pro Arg Tyr Ser Ala Lys Ala Leu Ala Arg Val Trp
                325                 330                 335

Lys Ser Glu Arg Phe Ser Trp Ser Leu Thr Lys Leu Met His Arg Phe
            340                 345                 350

Pro Glu Asp Gly Pro Phe Glu Arg Ala Met Gln Val Ala Glu Leu Glu
        355                 360                 365

Tyr Ile Ala Thr Ser Lys Ala Ala Gln Thr Ser Ile Ala Glu Asn Tyr
    370                 375                 380

Val Gly Leu Pro Val
385
```

<210> SEQ ID NO 5
<211> LENGTH: 528
<212> TYPE: DNA
<213> ORGANISM: Bordetella sp.
<220> FEATURE:
<221> NAME/KEY: CDS
<222> LOCATION: (1)..(525)
<223> OTHER INFORMATION: Codon-optimized oligonucleotide

<400> SEQUENCE: 5

-continued

```
atg atc atc ctg gaa aac ttc aag atg cca aac gtc gac ttg gaa gcc       48
Met Ile Ile Leu Glu Asn Phe Lys Met Pro Asn Val Asp Leu Glu Ala
1               5                   10                  15

gtg atg cgc tat ctt acc gag act ggc aaa cgc acc cat cag ctg tgg       96
Val Met Arg Tyr Leu Thr Glu Thr Gly Lys Arg Thr His Gln Leu Trp
            20                  25                  30

atg gat gat gag act ctc gca ttc gtt gct cgt ggt cgg gaa tat cgc      144
Met Asp Asp Glu Thr Leu Ala Phe Val Ala Arg Gly Arg Glu Tyr Arg
        35                  40                  45

tct gag ttc cac atc aat gcg tcc tac gag att cag tac tct ctg aaa      192
Ser Glu Phe His Ile Asn Ala Ser Tyr Glu Ile Gln Tyr Ser Leu Lys
    50                  55                  60

gga gcc caa gac ctc atg tat cgc aca cct gaa ggc gaa gtc aag gtg      240
Gly Ala Gln Asp Leu Met Tyr Arg Thr Pro Glu Gly Glu Val Lys Val
65                  70                  75                  80

gca cac atg cct gaa ggt tcc gtg ttt tac caa ccg cca ttc ctt ccg      288
Ala His Met Pro Glu Gly Ser Val Phe Tyr Gln Pro Pro Phe Leu Pro
                85                  90                  95

cat tca cct cgg ttt gca ccg gat agc ttc cag ttc atc att gag cga      336
His Ser Pro Arg Phe Ala Pro Asp Ser Phe Gln Phe Ile Ile Glu Arg
            100                 105                 110

gta cgc aaa cca ggg gaa atc gac aag ttc cac tgg ttt tgc ccc aat      384
Val Arg Lys Pro Gly Glu Ile Asp Lys Phe His Trp Phe Cys Pro Asn
        115                 120                 125

tgc gac aac ttc att cac gag gaa acc ttc tac gtc gac gat tac cgc      432
Cys Asp Asn Phe Ile His Glu Glu Thr Phe Tyr Val Asp Asp Tyr Arg
    130                 135                 140

aag gat ccc gtt tcg cgt gcg tac gac aac tac ttc aac tcc ctg gag      480
Lys Asp Pro Val Ser Arg Ala Tyr Asp Asn Tyr Phe Asn Ser Leu Glu
145                 150                 155                 160

ttt cgt acg tgc aag aag tgt ggc acc gtt gct cca gga cgc gat taa      528
Phe Arg Thr Cys Lys Lys Cys Gly Thr Val Ala Pro Gly Arg Asp
                165                 170                 175


<210> SEQ ID NO 6
<211> LENGTH: 175
<212> TYPE: PRT
<213> ORGANISM: Bordetella sp.

<400> SEQUENCE: 6

Met Ile Ile Leu Glu Asn Phe Lys Met Pro Asn Val Asp Leu Glu Ala
1               5                   10                  15

Val Met Arg Tyr Leu Thr Glu Thr Gly Lys Arg Thr His Gln Leu Trp
            20                  25                  30

Met Asp Asp Glu Thr Leu Ala Phe Val Ala Arg Gly Arg Glu Tyr Arg
        35                  40                  45

Ser Glu Phe His Ile Asn Ala Ser Tyr Glu Ile Gln Tyr Ser Leu Lys
    50                  55                  60

Gly Ala Gln Asp Leu Met Tyr Arg Thr Pro Glu Gly Glu Val Lys Val
65                  70                  75                  80

Ala His Met Pro Glu Gly Ser Val Phe Tyr Gln Pro Pro Phe Leu Pro
                85                  90                  95

His Ser Pro Arg Phe Ala Pro Asp Ser Phe Gln Phe Ile Ile Glu Arg
            100                 105                 110

Val Arg Lys Pro Gly Glu Ile Asp Lys Phe His Trp Phe Cys Pro Asn
        115                 120                 125

Cys Asp Asn Phe Ile His Glu Glu Thr Phe Tyr Val Asp Asp Tyr Arg
    130                 135                 140
```

```
Lys Asp Pro Val Ser Arg Ala Tyr Asp Asn Tyr Phe Asn Ser Leu Glu
145                 150                 155                 160

Phe Arg Thr Cys Lys Lys Cys Gly Thr Val Ala Pro Gly Arg Asp
                165                 170                 175


<210> SEQ ID NO 7
<211> LENGTH: 1863
<212> TYPE: DNA
<213> ORGANISM: Corynebacterium glutamicum

<400> SEQUENCE: 7

atgcgcgttt taattattga taattatgat tctttcacgt ttaatctcgc cacctatgtg     60

gaagaggtta cgggtcaggc acctgtggtg gtgcctaatg atcaagaaat agatgagatg    120

cttttcgacg ccgtcatcct ctcacctggc ccgggccacg ccggcgttgc ggctgatttt    180

ggtatctgtg caggcgtcat tgagcgtgca cgcgttccga ttttgggtgt gtgtttaggc    240

caccagggca ttgcgttggc ctatggcggt gatgttgatt tggcgcccag gccggtccac    300

ggtgaggttt cgcagatcac ccatgatggt tcaggtttat ttgcaggcat ccctgaaacg    360

tttgaggcgg tgcgttatca ctcgatggtg gcaacccgct tgccggagtc attgaaagct    420

acagctacca gcgatgatgg tttgatcatg gcattggcac atgaagtgct tccgcagtgg    480

ggtgtgcaat ttcatccgga atctattggt ggacaattcg gccatcagat cattaagaac    540

ttccttaatt tagcgcgcac atatcgctgg caactcacgg agaaaactat tccgctcagc    600

gttgattcag cagcggtttt tgaaacattc tttgcccatt cctcccatgc tttttggctc    660

gatgatgccc aaggaaccag ctatcttggt gatgccagcg gtcctctcgc acgcacaaaa    720

acccataatg tcggcgaggg ggatttcttc acctggctaa aggaggatct cgccgccaac    780

tcagttgcgc ccggtcaagg ttttcgtctt ggctgggttg gttacgttgg ttatgagctt    840

aaagcggaag ctggcgcacg ggctgcgcac acttcgagtc ttccggatgc gcacctcatt    900

tttgccgatc gcgccatcgc agtggaatcg gatcaggttc ggttgctggc gttgggggag    960

caggacgagt ggtttgaaga aaccatcaag aagctgcata atcttgtcgc cccgcggata   1020

cctgcgtccg gacacctcgc tttgcaggtt cgagattcca aagatgagta tctcgacaaa   1080

attcgcagag cccaggagct gattactcgc ggcgaatcgt atgaaatctg cctgaccaca   1140

aaacttcagg gcaccactga tgtggcccct ctggctgcct atctagcact gcgtggggcc   1200

aatcccaccg catatggtgc gtatcttcag ctgggggata cctctatttt gagttcctcg   1260

ccggagcggt tcatcaccat tgattcggca gggtatgtgg aatcaaagcc cattaaaggc   1320

accaggccgc gtgggcgaac agcgcaagaa gaccaagaaa tcattgctga gctgcgcagt   1380

aatcctaaag atcgtgcaga aaacttgatg atcgtggatt tggtccgcaa cgacttagcc   1440

cgcggcgctt tgcccaccac agttaaaaca tccaagcttt tcgacgtcga aacctacgcc   1500

acagtccacc aacttgtcag caccgtctct gcagagttgg ggccacgcag tccgattgag   1560

tgcgtgcgcg cagcattccc cggtggttcg atgactggtg ccccaaagct gcgcaccatg   1620

gagatcatcg atgagctgga ggcagctcct cgcggtattt actcaggtgg cttgggatat   1680

ttttccctcg acggcgcagt tgatctctcc atggtgatca gaactctcgt catccagaac   1740

aatcacgtgg agtacggagt gggcggtgca cttcttgctc tgtctgatcc ggaggctgag   1800

tgggaggaaa tccgcgttaa atcacggcct ctgctgaatt tgtttggggt tgaattccca   1860

tga                                                                  1863
```

-continued

<210> SEQ ID NO 8
<211> LENGTH: 726
<212> TYPE: DNA
<213> ORGANISM: Corynebacterium glutamicum

<400> SEQUENCE: 8
atgacgtacc tcgtgtggga cggtgcaaca ctcgtagaag gcgcgctgga atcaacaccc 60
acagttgttg attcctacct agccaaagac caccgcgtgg tgcgctggga tcttcatgaa 120
cagcgcttcg ccactagcgt ggacgtggac ccgtgggatt ttctccacgc agtaagggaa 180
gcaattccac gccagggctc atggtttccc aaagttgaat ggcatggcga tgatcttttc 240
gcagtcaata ttcgcccggc accaacactg cgaaaggcca catcattgtg gctttccgaa 300
gacccagatc cacgcacaca gccaaccatt aaaggcccag acctagatgt gcttgctcac 360
cttcgcagtc gcgccaacga taacggctgc gatgatgcgc tgttgatcag cgcggatggg 420
ttcattctgg aagctgccaa cgccaccgtg gtgttttggg cggatccaca gacggtcatc 480
gtgcccaggg gagatgtgct cccatcggtg acactcgccg caaccattcc gctgtgggaa 540
aaagccggaa tcacattgcg ctatcaaaac attcggcaca ttggttttcc cgcgtggtgc 600
ggtagttcgc tgcatggttg gacacctgtg gtcagttggg gcaggggatt gggcaaaatt 660
gcagcagcga aagctccatc ggtgaagccc tggaatgaaa aattgcgccc aaccattttt 720
ctgtaa 726

<210> SEQ ID NO 9
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 9
tattaattaa atgcgcgttt taattattga taattatgat tc 42

<210> SEQ ID NO 10
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 10
ttgcggccgc ttgtttaaac ctccttacag aaaaatggtt gggcg 45

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 11
aaatttaaac ctcctttaca gaaaaatggt tgg 33

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 12

-continued ggaggtttaa acaagcggcc gcgatatc 28

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 13
aggaggttta aatttatgcg cactcaggtg gctat 35

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
cttgtttaaa cctccttata cgagtggcag tccta 35

<210> SEQ ID NO 15
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 15
gctatcaaaa cattcggcac attggttttc c 31

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
ggaagatgcg tgatctgatc cttcaactc 29

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
ttacagaaaa atggttgggc gcaa 24

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 18
atgcgcactc aggtggctat cg 22

<210> SEQ ID NO 19
<211> LENGTH: 342
<212> TYPE: DNA
<213> ORGANISM: Artificial Sequence -continued
<220> FEATURE:
<223> OTHER INFORMATION: Synthetic oligonucleotide

<400> SEQUENCE: 19
tacgtacctg caggtagcgt gtcagtaggc gcgtagggta agtggggtag cggcttgtta 60
gatatcttga aatcggcttt caacagcatt gatttcgatg tatttagctg gccgttaccc 120
tgcgaatgtc cacagggtag ctggtagttt gaaaatcaac gccgttgccc ttaggattca 180
gtaactggca cattttgtaa tgcgctagat ctgtgtgctc agtcttccag gctgcttatc 240
acagtgaaag caaaaccaat tcgtggctgc gaaagtcgta gccaccacga agtccaaagg 300
aggatctaaa ttatgaataa tataaaagga ggaattaatt aa 342

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 20 accattttc tgtaatacgt acctgcaggt agcgtg 36

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
cacctgagtg cgcatttaat taattcctcc tttta 35

<210> SEQ ID NO 22
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 22
gcttgttaga tatcttgaaa tcggctttc 29

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
ggaggtttaa acaagcgg 18

<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 24
aatttagatc ctcctttgga cttcgtg 27

<210> SEQ ID NO 25

-continued

<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 25
aggaggatct aaattatgcg cactcaggtg gctatc 36

<210> SEQ ID NO 26
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 26
cttgtttaaa cctccttata cgagtggcag tcctacg 37

<210> SEQ ID NO 27
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 27
cgcttgttta aacctcctta tacgagtggc agtcctacg 39

<210> SEQ ID NO 28
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 28
gccgcgatat cgttgtaaaa aaccccgctc 30

<210> SEQ ID NO 29
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 29
aggtttaaac aagcgatgat catcctggaa aacttcaaga tg 42

<210> SEQ ID NO 30
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 30
caacgatatc gcggcttaat cgcgtcctgg agcaac 36